(12) United States Patent
Green

(10) Patent No.: US 7,170,594 B2
(45) Date of Patent: Jan. 30, 2007

(54) DEVICE FOR POLYMERASE CHAIN REACTIONS

(75) Inventor: Douglas Jason Green, Baldwin, MD (US)

(73) Assignee: Smiths Detection, Inc., Edgewood, MD (US)

( * ) Notice: Subject to any disclaimer, the term of this patent is extended or adjusted under 35 U.S.C. 154(b) by 0 days.

(21) Appl. No.: 10/837,745

(22) Filed: May 4, 2004

(65) Prior Publication Data

US 2005/0002024 A1 Jan. 6, 2005

Related U.S. Application Data

(60) Provisional application No. 60/473,447, filed on May 28, 2003.

(51) Int. Cl.
*G01N 1/10* (2006.01)
(52) U.S. Cl. ..................................................... 356/246
(58) Field of Classification Search ..................... None
See application file for complete search history.

(56) References Cited

U.S. PATENT DOCUMENTS

| | | | |
|---|---|---|---|
| 2,543,825 A | * | 3/1951 | Beu et al. ...................... 378/80 |
| 4,443,407 A | * | 4/1984 | Weinberg et al. ........ 422/82.04 |
| 4,848,093 A | * | 7/1989 | Simmonds et al. .......... 62/49.1 |
| 5,589,136 A | | 12/1996 | Northrup et al. |
| 6,191,599 B1 | | 2/2001 | Stevens |
| 6,403,037 B1 | | 6/2002 | Chang et al. |
| 6,440,725 B1 | | 8/2002 | Pourahmadi et al. |
| 6,521,181 B1 | | 2/2003 | Northrup et al. |
| 6,524,532 B1 | | 2/2003 | Northrup |
| 6,565,815 B1 | | 5/2003 | Chang et al. |
| 6,602,473 B1 | | 8/2003 | Northrup |

FOREIGN PATENT DOCUMENTS

WO WO 97/27324 7/1997

OTHER PUBLICATIONS

PCT International Search Report (4 pgs.).

* cited by examiner

*Primary Examiner*—Tu T. Nguyen
(74) *Attorney, Agent, or Firm*—Foley & Lardner LLP

(57) ABSTRACT

A detection device includes a housing containing a chamber configured to receive a specimen, a heating element disposed in the chamber, and an optical window to permit observation of the chamber. The housing includes a passage configured to allow fluid flow through the chamber to thereby provide cooling.

30 Claims, 5 Drawing Sheets

DEVICE FOR POLYMERASE CHAIN REACTIONS

CROSS-REFERENCE TO RELATED PATENT APPLICATIONS

This application claims priority to and the benefit of U.S. Provisional Application No. 60/473,447, filed May 28, 2003, which is incorporated by reference herein.

BACKGROUND

The present invention relates to a device for a Polymerase Chain Reaction (PCR) and, more particularly, to a device that can be used in conjunction with a handheld instrument to detect the presence or absence of a biological agent in a sample using PCR technology.

PCR technology can be used by facility security professionals, military forces, and first responders, such as fire fighters, police, emergency medical personnel, and HAZMAT teams, to determine whether a life threatening biohazard is present at locations on-site and in the field. For example, a biological detection instrument utilizing PCR technlology can be used to test a sample for the presence of a biological agent, such as anthrax, providing accurate results in forty minutes or less.

The sample is first formulated into a PCR reaction mixture in a disposable reaction tube. The reaction tube is inserted into a chamber in a reaction device in the instrument. In the reaction device, the reaction mixture undergoes thermal cycling (heating and cooling). The presence or absence of the biological agent is optically detected by the instrument.

One disadvantage of conventional reaction devices is that such reaction devices are too heavy and complex to be packaged into a portable (handheld) biological detection instrument that is suitable for use on-site and in the field. For example, a conventional reaction device consists of a metal block through which heating and cooling fluids are passed to heat and cool the reaction mixture (see, e.g., U.S. Pat. No. 5,555,675, incorporated by reference herein). The metal block and the components necessary for controlling fluid temperature and supply increase the weight and complexity of the reaction device. As a result, the weight and complexity of the biological detection instrument increases so that the instrument can not be easily transported to on-site and field locations.

Another disadvantage of conventional reaction devices is that such reaction devices can not heat and cool the reaction mixture rapidly or efficiently. For example, the metal block of a conventional reaction device has a high coefficient of thermal conductivity so that heat is conducted away from the reaction mixture through the metal block back into the instrument. Thus, the heating efficiency of the reaction device is reduced. As a result, a time period for completing a thermal cycle is increased.

Although some conventional reaction devices employ micro-machined silicon with an integrated heating element to rapidly heat and cool the reaction mixture, such reaction devices suffer from relatively high tooling, labor, and production costs (see, e.g., U.S. Pat. No. 5,589,136, incorporated by reference herein). Additionally, the fragility of micro-machined heaters makes such heaters impractical for portable field use.

SUMMARY OF THE INVENTION

According to an aspect of the present invention, a detection device is provided. The detection device includes a housing containing a chamber configured to receive a specimen, a heating element disposed in the chamber, and an optical window to permit observation of the chamber. The housing includes a passage configured to allow fluid flow through the chamber to thereby provide cooling.

According to another aspect of the present invention, an instrument for detecting a biological agent is provided. The instrument includes a plurality of housings arranged in an array. Each housing includes a chamber configured to receive a specimen, a heating element disposed in the chamber, and an optical window to permit observation of the chamber. Additionally, each housing includes a passage configured to allow fluid flow through the chamber to thereby provide cooling.

BRIEF DESCRIPTION OF THE DRAWINGS

The accompanying drawings, which are incorporated in and constitute a part of this specification, illustrate embodiments of the invention and together with the description serve to explain the principles of the invention.

DETAILED DESCRIPTION

Figure 1:
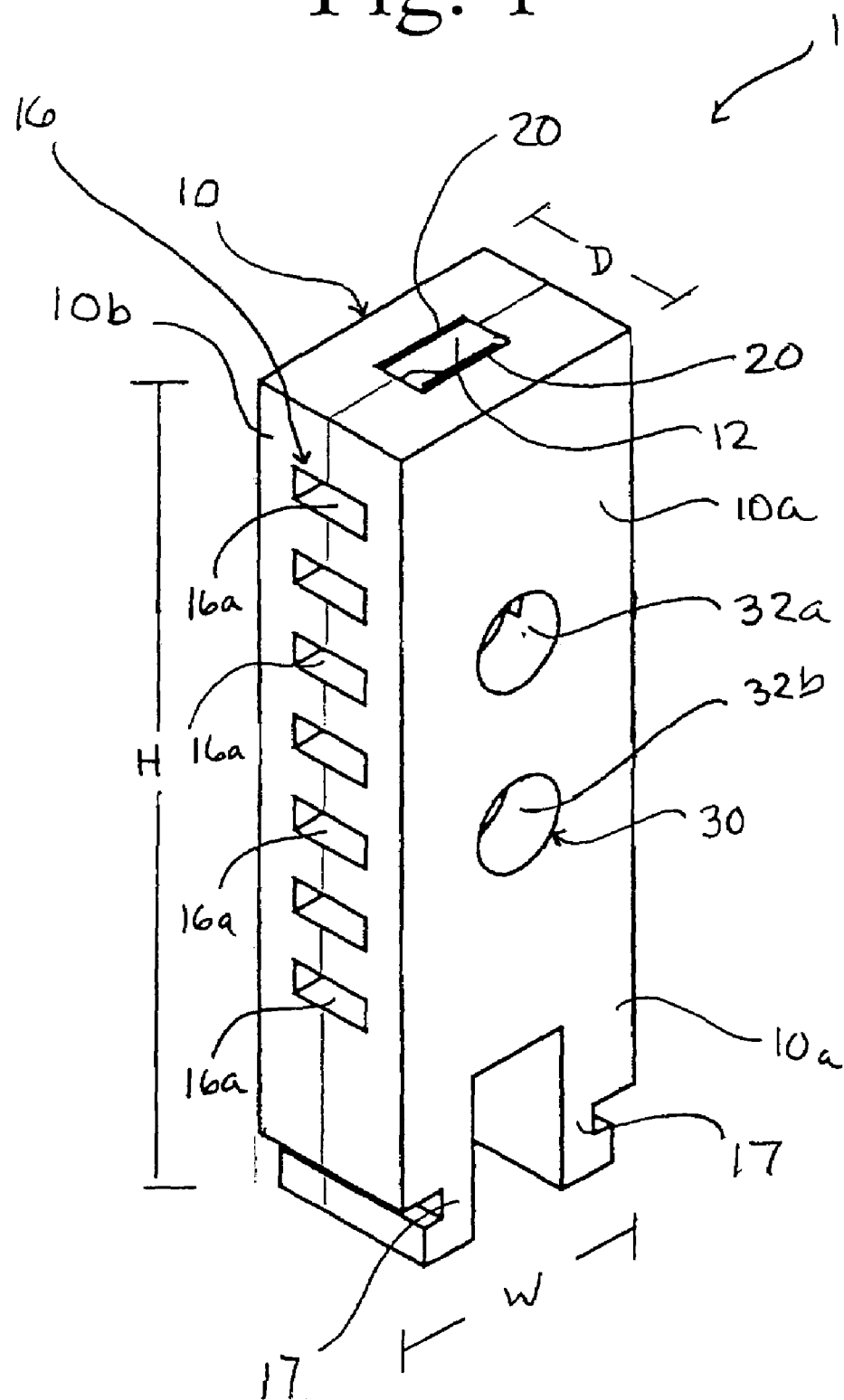
FIG. 1 is a perspective view of an embodiment of a detection device according to the present invention.

Referring to FIG. 1, a detection device 1 for an instrument 40 generally includes a housing 10, a heating element 20, and an optical aperture (window) 30.

The housing 10 is configured to receive a specimen (sample) that potentially contains a biological agent, such as anthrax, tularemia, plague, or smallpox. The specimen may be contained within a disposable reaction tube having an elongated portion that can be inserted into the housing 10. The reaction chamber 1 is preferably used in combination with reaction tubes (sample holders) as described in U.S. patent application Ser. No. 10/737,037, filed Dec. 4, 2003, and U.S. Provisional Patent Application No. 60/473,539, filed May 28, 2003, incorporated by reference herein.

As shown in FIG. 1, the housing 10 may be shaped so that a height H of the housing 10 is greater than a width W of the housing 10. The height H may also be greater than a depth D of the housing 10. Thus, the housing 10 has a rectangular shape. A bottom portion of the housing 10 includes a pair of legs 17 to facilitate insertion of the housing 10 into a mounting rail of the instrument 40.

Figure 3:
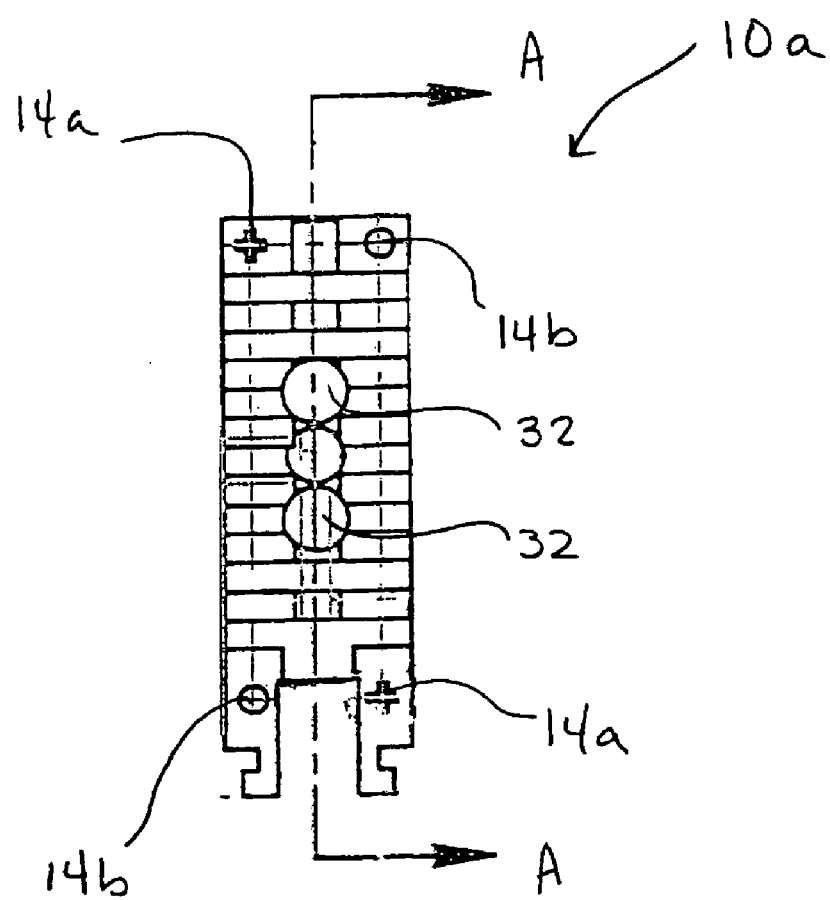
FIG. 3 is an elevational view of a first portion of the detection device of FIG. 1.

The housing 10 includes a first portion 10a (shown in FIG. 3) and a second portion 10b connected together to form a chamber 12, which is configured to receive the specimen. The second portion 10b is structurally similar to the first portion 10a (except the second portion 10b lacks an optical aperture 30) and is configured to mate with the first portion 10a. The first portion 10a and the second portion 10b may be connected together in any conventional manner (e.g., using an adhesive) but are preferably configured to snap together. For example, the first portion 10a and the second portion 10b may each include one or more tangs 14a (shown in FIGS. 4 and 5) that are configured to snap into engagement with corresponding apertures 14b disposed on the other portion 10a or 10b of the housing 10.

Figure 4:
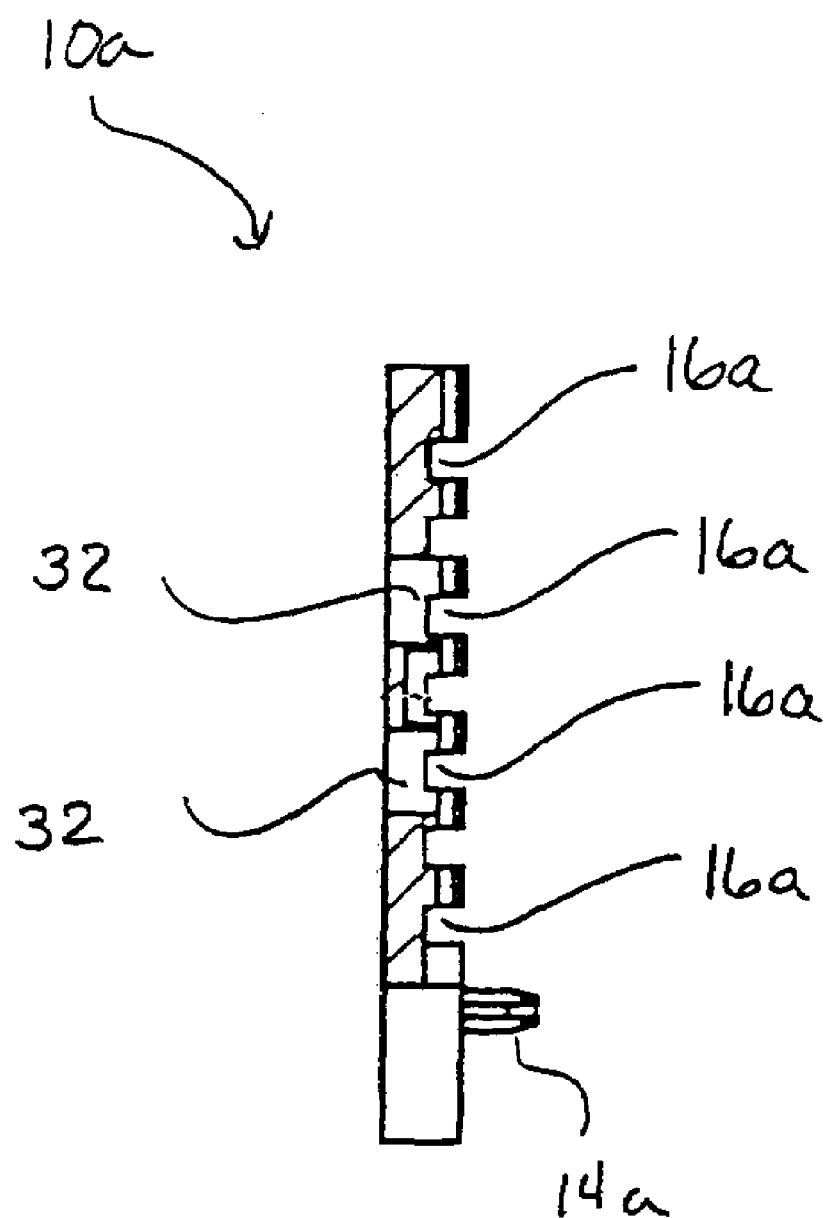
FIG. 4 is a sectional view taken along the line A—A of FIG. 3.
Figure 5:
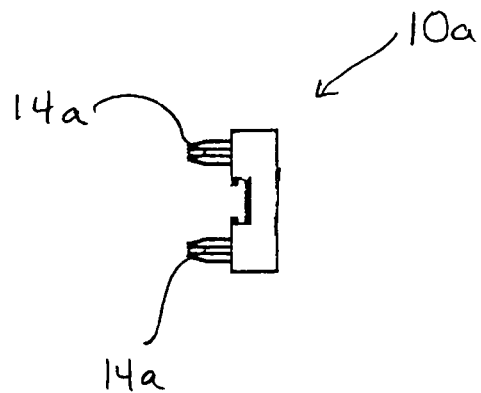
FIG. 5 is a top plan view of the first portion of the detection device of FIG. 1.

The housing 10 also includes a passage 16 configured to allow fluid flow through the chamber 12 to provide cooling. For example, the passage 16 may include a plurality of channels 16a disposed one above the other, as shown in FIG. 1. Each channel 16a preferably extends from a first side of the housing 10 to a second side of the housing 10. Thus, the channels 16a extend completely through the housing 10 (as shown in FIG. 4). Additionally, the channels 16a intersect with the chamber 12 so that the fluid flows past the specimen when the specimen is received in the chamber 12. In this manner, a fluid, such as air, can flow through the chamber 12 to thereby remove heat and provide cooling to the specimen.

According to an embodiment of the invention, the housing 10 is made of an electrically insulating material. The material can be, for example, a plastic, a polymer, or a resin and can have a thermal conductivity of less than approximately 1 W/m-K. Preferably, the housing 10 is formed of a thermoplastic polyester resin, such as a resin known by the brand name VALOX®. According to another embodiment of the invention, the housing 10 is formed from a thermally insulating material. As a result, the heating element 20 is insulated from the instrument 40 by the housing 10 so that an amount of heat conducted through the housing 10 to the instrument 40 is substantially reduced. Thus, heat generated by the heating element 20 is focused on the specimen. Preferably, the housing 10 is formed of a material that is both electrically and thermally insulating. VALOX® is an exemplary material. The use of plastic, polymer, or resin material to form the housing 10 reduces the weight of the housing 10 relative to a weight of a conventional device made of a metal block. As a result, the detection device 1 has improved thermal efficiency, lower cost, and is more portable and easier to handle.

The heating element 20 provides heat to the chamber 12 so that a temperature of the specimen can be increased when the specimen is inserted in the chamber 12. The heating element 20 may be flexible and may have a thickness, for example, of approximately 0.015 inches or less. In an exemplary embodiment, the heating element 20 is a thin film resistor that includes two etched resistance elements 22 (heaters) deposited on a substrate 21. The substrate 21 may be a polyester film, such as the polyester film known by the brand name MYLAR®, or a polyimide film, such as the polyimide film known by the brand name KAPTON®. The heating element 20 may also include a thermistor 23 for sensing a temperature of the heating element 20.

Figure 2:
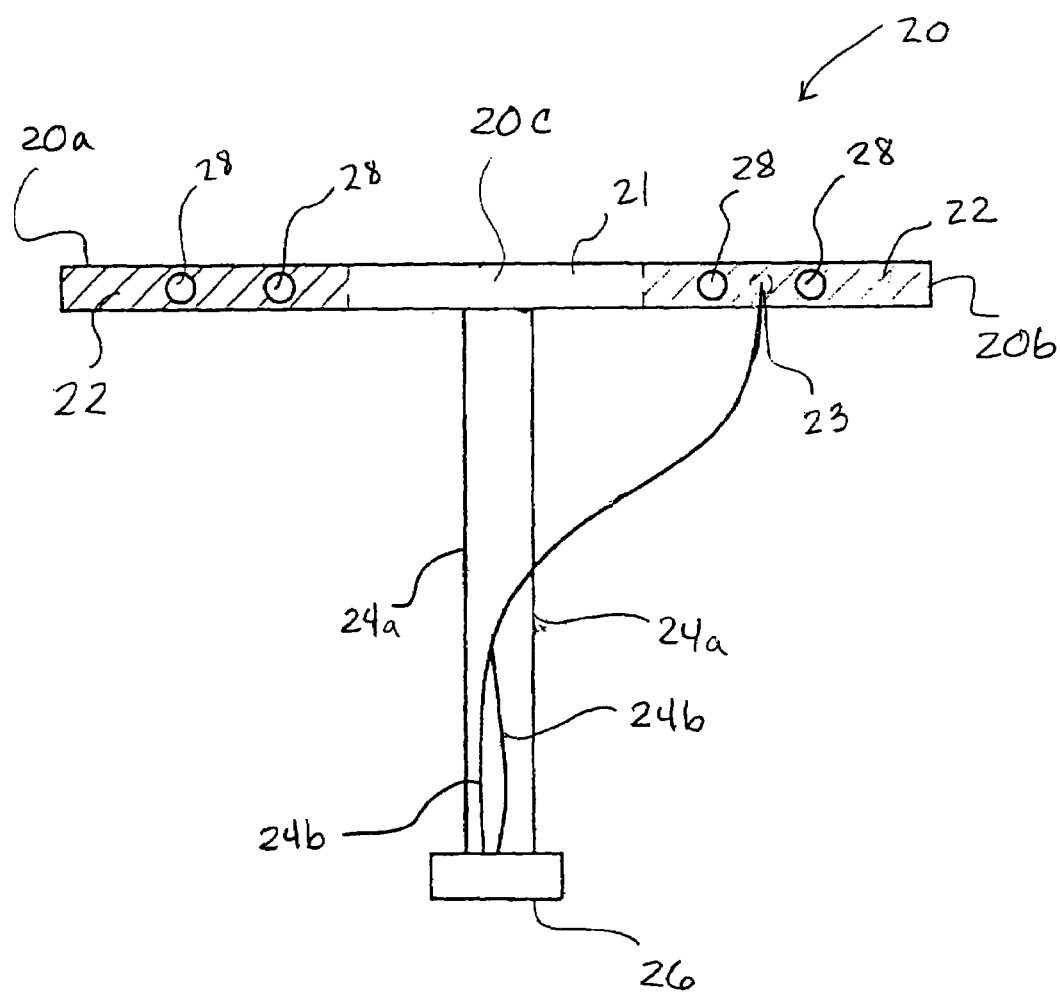
FIG. 2 is a top plan view of a heating element of the detection device of FIG. 1.

The heating element 20 (shown in FIG. 2) is configured to be disposed in the chamber 12 on a wall of the chamber 12. The heating element 20 may be, for example, bonded to a wall of the chamber 12 using an adhesive. In an exemplary embodiment, the heating element 20 is a unitary assembly that is attached to the housing 10 before the first portion 10a and the second portion 10b of the housing are mated together. In this embodiment, one end 20a of the heating element 20 is attached to the first portion 10a of the housing, and the other end 20b of the heating element 20 is attached to the second portion 10b of the housing. A central portion 20c of the heating element 20 is configured to fold so that the first and second portions 10a, 10b of the housing 10 can then be connected. In this manner, the heating element 20 is installed within the chamber 12 of the housing 10.

The heating element 20 is configured to connect to a power source in the instrument 40. For example, the heating element 20 may include lead wires 24a for the resistance element 22 and lead wires 24b for the thermistor 23. One end of each of the lead wires 24a, 24b can be crimped or bonded to the heating element 20, and the other end of each of the lead wires 24a, 24b can terminate at a connector 26 (e.g., a wire-to-wire receptacle) for connection to the power source. The heating element 20 can additionally include openings 28 that comprise a part of the optical aperture 30.

The optical aperture 30 is configured to permit optical monitoring or observation of the chamber 12 by the instrument 40. As shown in FIGS. 1 and 4, the optical aperture 30 includes a first opening 32a and a second opening 32b extending through a wall of the housing 10. The openings 32a and 32b may be located, for example, one above the other so that the first opening 32a is disposed above the second opening 32b. When the heating element 20 is installed in the housing 10, the openings 28 of the heating element are aligned with the openings 32a and 32b so that the optical aperture 30 extends through the heating element 20. Thus, the heating element 20 does not obstruct a viewing path into the chamber 12 of the optical aperture 30.

The optical aperture 30 is arranged to enable a detector in the instrument 40 to analyze the specimen when the specimen is inserted in the chamber 12 of the detection device 1. The detector determines whether a biological agent is present in the specimen using optical spectroscopy. The detector may be any suitable detector but is preferably a detector that uses fluorescence-based optical spectroscopy. In operation, a user formulates a sample into a PCR reaction mixture in a disposable reaction tube and inserts the reaction tube into the chamber 12 of the detection device 1. In the detection device 1, DNA amplification is accomplished by subjecting the reaction mixture to a series of thermal cycles (e.g., 40 to 50 thermal cycles). According to an exemplary embodiment, during each thermal cycle, the detection device 1 heats the reaction mixture to a temperature of approximately 96 degrees Celsius by activating the heating element 20 and then cools the temperature of the reaction mixture to a temperature of approximately 60 degrees Celsius by deactivating the heating element 20 and permitting air to flow through the channels 16a. The air flow is preferably a forced air flow powered by an air source such as a fan. When the thermal cycling is complete, an excitation wavelength is directed through one of the openings 32a, 32b and a detection (emission) wavelength is directed through the other of the openings 32a, 32b to thereby determine whether the biological agent is present in the reaction mixture. An increase of emitted fluorescence is associated with the presence of the biological agent.

Figure 6:
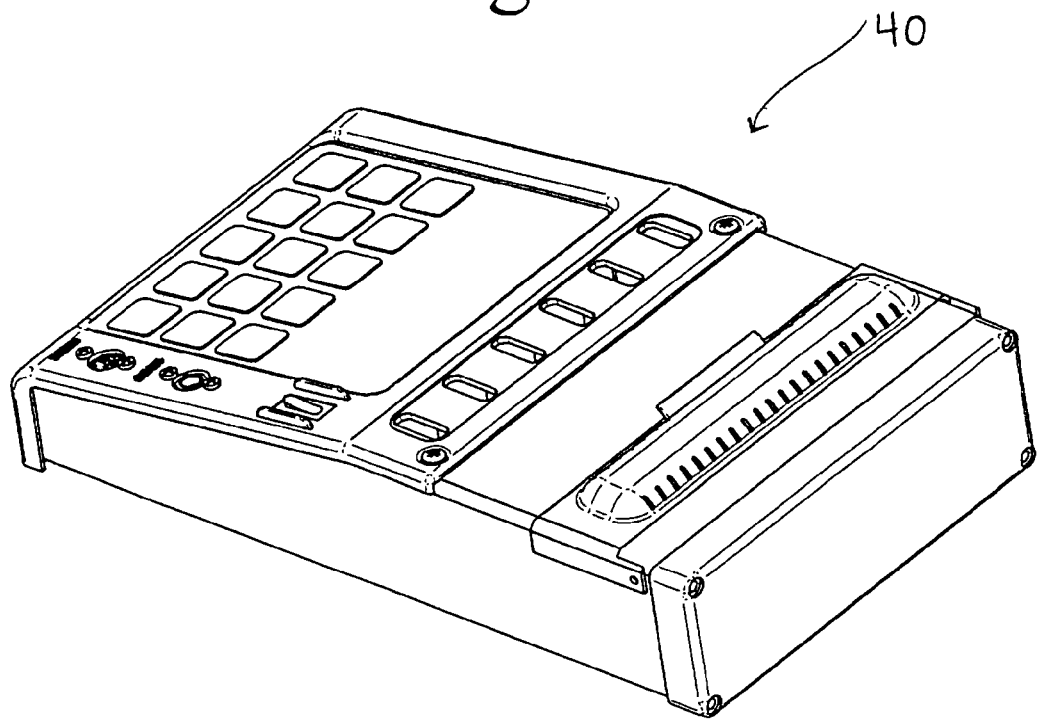
FIG. 6 is a perspective view of an embodiment of a portable detection instrument according to the present invention.

The above-described embodiments of the detection device 1 may be used in combination with an instrument 40 (shown in FIG. 6) that is lightweight and handheld. In an exemplary embodiment, the instrument 40 includes several independently operated detection devices 1 arranged in an array, as shown in FIG. 6, so that multiple samples may be analyzed simultaneously. In this manner, PCR technology for detecting biohazards is made readily available to facility security professionals, military forces, and first responders at locations on-site and in the field.

Thus, according to the exemplary embodiments described above, a device that can be used in conjunction with a handheld instrument to detect the presence or absence of a biological agent in a sample using PCR technology is provided.

Modifications and other embodiments of the invention will be apparent to those skilled in the art from consideration of the specification and practice of the invention disclosed herein. It is intended that the specification and examples be considered as exemplary only, the scope of the invention being limited only by the appended claims.

What is claimed is:

1. A detection device comprising:
   a housing comprising a thermal insulator and a chamber configured to receive a specimen;
   a heating element disposed in the chamber; and
   an optical window to permit observation of the chamber,
   wherein the housing includes a passage configured to allow fluid flow through the chamber to thereby provide cooling, and
   wherein the fluid is air.

2. The detection device of claim 1, wherein the housing comprises an electrical insulator.

3. The detection device of claim 1, wherein the housing comprises plastic.

4. The detection device of claim 1, wherein the housing comprises a polymer material.

5. The detection device of claim 1, wherein the housing comprises a resin.

6. The detection device of claim 5, wherein the resin comprises a thermoplastic polyester resin.

7. The detection device of claim 1, wherein the thermal insulator has a thermal conductivity of less than approximately 1 W/m-K.

8. The detection device of claim 1, wherein a height of the housing is greater than a width of the housing and greater than a depth of the housing.

9. The detection device of claim 1, wherein the housing includes a first portion and a second portion connected together to form the chamber.

10. The detection device of claim 9, wherein the first portion and the second portion are configured to snap together.

11. The detection device of claim 10, wherein the first portion includes a projection and the second portion includes an aperture, and wherein the projection and the aperture are configured to engage so that the first portion and the second portion can snap together.

12. The detection device of claim 1, wherein the heating element comprises a thin film resistor.

13. The detection device of claim 12, wherein the thin film resistor includes an etched resistance element deposited on a substrate.

14. The detection device of claim 13, wherein the substrate comprises a polyester film.

15. The detection device of claim 13, wherein the substrate comprises a polyimide film.

16. The detection device of claim 1, wherein the heating element is flexible.

17. The detection device of claim 1, wherein the heating element comprises a first heater and a second heater.

18. The detection device of claim 17, wherein the first heater is disposed on a first wall of the chamber and the second heater is disposed on a second wall of the chamber opposite the first wall.

19. The detection device of claim 1, wherein the passage comprises a plurality of channels disposed one above the other.

20. The detection device of claim 1, wherein the passage extends from a first side of the housing to a second side of the housing.

21. The detection device of claim 1, wherein the optical window is configured to enable optical monitoring of the chamber by the detection device.

22. The detection device of claim 1, wherein the optical window comprises an opening extending through a wall of the housing.

23. The detection device of claim 1, wherein the optical window includes an opening extending through the heating element.

24. The detection device of claim 22, wherein the opening comprises a first opening and a second opening disposed below the first opening.

25. The detection device of claim 1, wherein the detection device is configured to detect fluorescence of the specimen.

26. The detection device of claim 1, wherein the specimen is contained within a reaction tube.

27. The detection device of claim 26, wherein the reaction tube is configured to be received in the chamber.

28. A portable instrument for detecting a biological agent, comprising:
   a plurality of housings arranged in an array,
   wherein each housing comprises a thermal insulator, a chamber configured to receive a specimen, a heating element disposed in the chamber, and an optical window to permit observation of the chamber,
   wherein each housing includes a passage configured to allow fluid flow through the chamber to thereby provide cooling, and
   wherein the fluid is air.

29. The portable detection device of claim 28, wherein the portable instrument is configured to be held in a hand of a user.

30. The portable detection device of claim 28, wherein the portable instrument includes six housings.

* * * * *